(12) United States Patent
Weaver et al.

(10) Patent No.: US 7,487,739 B1
(45) Date of Patent: Feb. 10, 2009

(54) SUBLIMATION CONTAINMENT APPARATUS AND METHOD FOR DEVELOPING LATENT FINGERPRINTS

(76) Inventors: David M. Weaver, P.O. Box 179, Lookout, WV (US) 25868; Ordis G. Weaver, 6107 W. Bogart Rd., Castalia, OH (US) 44824

( * ) Notice: Subject to any disclaimer, the term of this patent is extended or adjusted under 35 U.S.C. 154(b) by 0 days.

(21) Appl. No.: 11/564,605

(22) Filed: Nov. 29, 2006

Related U.S. Application Data

(60) Provisional application No. 60/817,167, filed on Jun. 27, 2006, provisional application No. 60/740,953, filed on Nov. 29, 2005.

(51) Int. Cl.
*A61B 5/117* (2006.01)
*C23C 16/00* (2006.01)
*C23C 16/448* (2006.01)
*C23C 16/455* (2006.01)

(52) U.S. Cl. .................. 118/31.5; 118/715; 118/726
(58) Field of Classification Search ................ 118/31.5, 118/715, 726; 427/1
See application file for complete search history.

(56) References Cited

U.S. PATENT DOCUMENTS

| 4,297,383 | A | * | 10/1981 | Bourdon ..................... 427/1 |
| 4,556,579 | A | | 12/1985 | Lowell |
| 4,613,515 | A | | 9/1986 | Reggio |
| 5,266,112 | A | * | 11/1993 | Crosbie ..................... 118/31.5 |
| 5,281,293 | A | | 1/1994 | Frame et al. |
| 5,342,645 | A | | 8/1994 | Eisele et al. |
| 5,348,759 | A | * | 9/1994 | Weaver et al. .................. 427/1 |
| 5,395,445 | A | * | 3/1995 | Bohanan ..................... 118/31.5 |
| 5,424,092 | A | * | 6/1995 | Weaver et al. .................. 427/1 |
| 5,906,871 | A | | 5/1999 | Takebe et al. |
| 6,423,946 | B1 | * | 7/2002 | Berka et al. .................. 219/390 |
| 6,660,054 | B2 | * | 12/2003 | Manna et al. .............. 55/385.2 |
| 7,323,207 | B2 | * | 1/2008 | Nichols et al. ................. 427/1 |
| 2005/0252444 | A1 | * | 11/2005 | Nichols et al. ............ 118/31.5 |
| 2007/0026130 | A1 | * | 2/2007 | Arndt ............................ 427/1 |

FOREIGN PATENT DOCUMENTS

| JP | 2-268744 | * | 2/1990 |
| WO | WO 94/26166 | * | 11/1994 |

* cited by examiner

Primary Examiner—Jeffrie R Lund
(74) Attorney, Agent, or Firm—Thompson Hine LLP

(57) ABSTRACT

An apparatus and method for developing latent fingerprints having a heat source with a removably mounted chamber and sublimation system wherein the sublimation system is in communication with a heat emitting end of the heat source and an internal space of the chamber. Upon activating the heat source, heat transforms a cyanoacrylate of the sublimation system into vapor within the internal space of the chamber. The vapor contacts an object contained within the chamber to reveal any latent fingerprints on the object.

14 Claims, 4 Drawing Sheets

SUBLIMATION CONTAINMENT APPARATUS AND METHOD FOR DEVELOPING LATENT FINGERPRINTS

CROSS-REFERENCE TO RELATED APPLICATION

This application claims the benefit of U.S. Application No. 60/740,953 filed on Nov. 29, 2005, and U.S. Application No. 60/817,167 filed on Jun. 27, 2006.

BACKGROUND

1. Technical Field

The present invention relates to apparatuses for developing latent fingerprints and the method of use thereof, and in particular, to the use of a chamber in combination with a heat source and a sublimation system containing a cyanoacrylate wherein the application of heat transforms the cyanoacrylate to vapor which is used in the quick and efficient development of latent fingerprints on objects contained in the chamber.

2. Related Art

The use of cyanoacrylate in the development of latent fingerprints on objects is well known and has been used as such for many years. Specifically, it is the reaction of the cyanoacrylate monomer and a catalyst that creates a microcrystalline vapor which adheres to fingerprints. Once the vapor cures, the cyanoacrylate forms a white polymer substance that reveals the fingerprint.

U.S. Pat. No. 4,556,579 to Lowell discloses a kit for developing latent fingerprints wherein liquid cyanoacrylate monomer is deposited onto a porous fiber plug made of cellulose acetate fibers. The resulting fumes from the chemical reaction generate any latent fingerprints that come into contact with the fumes. The kit also has a solvent for removing such fingerprints when desired.

Similar to the '579 patent, U.S. Pat. No. 4,613,515 to Reggio also discloses a kit for developing latent fingerprints on a solid surface. The kit contains an absorbent pad impregnated with a cyanoacrylic polymerization catalyst and one or more initiators, a promoter and an accelerator. The kit also provides a separate source of a polymerizable alpha-cyanoacrylate monomer with at least one inhibitor agent. In operation, a cyanoacrylate monomer is added to the surface of the pad and the pad is placed adjacent a surface believed to contain a fingerprint. The pad remains undisturbed until it generates a microcrystalline vapor from the reaction of the cyanoacrylic catalyst and monomer. The vapor travels through the air to the solid surface wherein upon contact with the surface it adheres to the latent fingerprint, thereby making the latent fingerprint visible.

There are several disadvantages with the kits of the '579 and '515 patents. The user must physically add the cyanoacrylate monomer to a pad or plug which may result in unwanted spillage or a wrong amount of cyanoacrylate monomer applied to the pad. The kits also consist of multiple components which increases the complexity of using the kits as well as increases the amount of waste.

U.S. Pat. No. 5,342,645 to Eisele, et al. discloses a metal cartridge containing a porous or fibrous pad such as steel or glass wool, impregnated with a cyanoacrylate ester and a volatile, emissive lanthanide metal-complex or actinide metal-complex. Upon the application of heat, e.g., a butane-powered torch, the chemical reaction produces a chemical vapor that is used to develop latent fingerprints. The principal disadvantages with the '645 patent is that it requires a heat resistent housing and the use of a butane torch, both requirements making the cartridge clumsy and potentially dangerous to use.

U.S. Pat. Nos. 5,348,759 and 5,424,092 to Weaver, et al. disclose a device for developing latent fingerprints. The device has a housing that contains a cyanoacrylate (either in liquid or solid form) and is adapted to receive a propane torch. Upon lighting the torch, the cyanoacrylate is vaporized and propelled toward the object to be tested on which any latent fingerprints appear within minutes. The user may replace the cyanoacrylate as needed for new tests. The disadvantage with these devices is that they require the use of a propane torch which increases the potential danger of using the devices. The devices also have multiple components including the need for additional cyanoacrylate to refill the housing, which increases the maintenance of the devices.

U.S. Pat. No. 5,395,455 to Bohanan discloses a method and apparatus for developing latent fingerprints on a portion of skin. The apparatus uses a heater to create a cyanoacrylate vapor which is propelled by a fan through a hose and comes in contact with skin. As seen in previous devices, this apparatus is very cumbersome to carry and use in field operation, and requires the use of a separate heater and fan which increases the maintenance effort.

U.S. Pat. No. 6,423,946 to Berka, et al. discloses an apparatus for developing latent fingerprints having a sealable container for depositing objects being tested for fingerprints. The container has an electrical heater as well as an exhaust means for evacuating air from the internal chamber. In operation, the method includes heating the container, placing objects within the chamber, adding a few drops of cyanoacrylate on an upper surface of an internal receptacle, covering the container, and pumping air from the container. After the fumes have developed any latent fingerprints on the objects within the chamber, the cover is removed and the objects are taken out. The disadvantage with the '946 device is that it is cumbersome to carry and use in the field. The user requires an electrical outlet for powering the heater. Also, the internal size of the chamber limits the number, size, and shape of the objects that can be placed in the container for testing.

Therefore, upon review of the prior art, there is a need for a simple, self-contained, re-chargeable apparatus for developing latent fingerprints. There is a further need for such an apparatus having a containment system for directing the fumes or vapors toward and around the object being examined.

BRIEF DESCRIPTION OF THE DRAWINGS

The present invention is described with reference to the accompanying drawings. In the drawings, like reference numbers indicate identical or functionally similar elements. Additionally, the left-most digit(s) of a reference number identifies the drawings in which the reference number first appears.

DETAILED DESCRIPTION OF THE INVENTION

Figure 1:
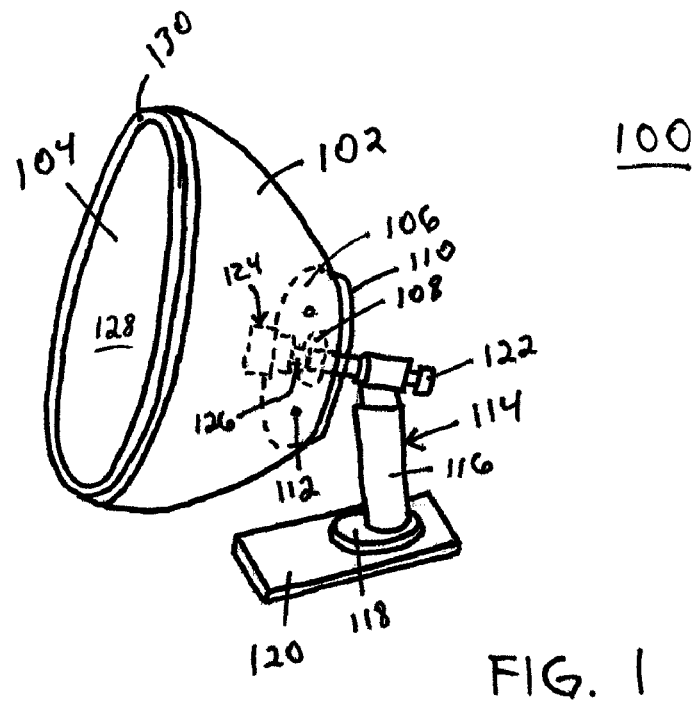
FIG. 1 is a perspective view of an apparatus of the present invention.

As shown in FIG. 1, the present invention is an apparatus 100 having a heat source 114, a sublimation system 124, and a chamber 102. The heat source 114 has a heat emitting end 126 that is in communication with the internal space 128 of the chamber 102, and preferably extends into the internal space 128. The sublimation system 124 is in communication with the heat emitting end 126 of the heat source 114, and preferably is removably attached to the heat emitting end 126.

In the preferred embodiment, the heat source 114 is a commercially available pressurized fuel system, such as a butane canister fuel system, having a handle 116 for storing a pressurized can of butane fuel, an on/off button 122, and a first base 118 affixed to a larger second base 120 which is sized such that the apparatus 100 stands in a substantially upright position when the second base 120 is placed on a level surface. The heat emitting end 126 of the heat source 114 is joined to the handle 116 such that expelled fuel from the can of pressurized fuel flows through and exits from the heat emitting end 126 of the heat source 114 in an ignited/heated state. In operation, a user places a can of pressurized fuel in the handle 116, and upon activating the on/off button 122, a flame, or heat, is expelled from the heat emitting end 126.

The use of a pressurized fuel system as the heat source 114 is for convenience only. It would be readily apparent to use alternative heat sources 114, such as, any replaceable fuel canister system, a torch system, a forced air heat system, and an electric heat system with a fan.

Figures 2A, 2B:
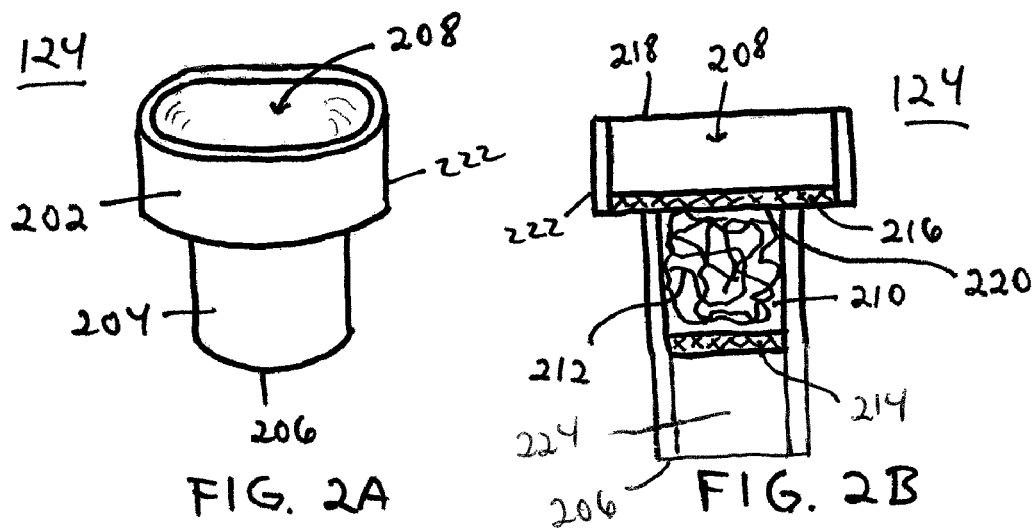
FIG. 2A is a perspective view of sublimation cartridge of the present invention.
FIG. 2B is a planar cut-away cross sectional view of the sublimation cartridge.

The preferred sublimation system 124 is shown in greater detail in FIGS. 2A and 2B. In the preferred embodiment, the sublimation system 124 is a hollow sublimation cartridge 222 having a first end 218, a second end 206, a head 202, a head cavity 208, a throat 204, and a throat cavity 210 wherein the diameter of the head cavity 208 is greater than the diameter of the throat cavity 210. The first end 218 of the sublimation cartridge 222 is in communication with the internal space 128 of the chamber 102, and in the preferred embodiment, the first end 218 of the sublimation cartridge 222 is disposed within the internal space 128 of the chamber 102.

The sublimation cartridge 222 is preferably made of metal, ceramic, or glass and is about 1-2 inches in length. The sublimation cartridge 222 contains the components needed to create the cyanoacrylate vapors 306 used in developing latent fingerprints. In this first embodiment, a porous pad 212, such as a ball of steel wool, ceramic fiber, granulated loose wool, and non-granulated loose wool, is disposed within the throat cavity 210 between a first retaining screen 216 and a second retaining screen 214. The first and second retaining screens 216, 214 are preferably made of bronze metal, but this is for convenience wherein any high temperature resistance material is suitable. The first retaining screen 216 is positioned at the intersection 220 of the head 202 and throat 204, whereas the second retaining screen 214 is positioned at a point within the throat 204. The positioning of the first retaining screen 216 and the second retaining screen 214 are also for convenience.

Liquid cyanoacrylate is deposited on the porous pad 212 and allowed to dry. The second end 206 of the sublimation cartridge 222 is sized such that it slides onto the heat emitting end 126 of the heat source 114 and is pressure fit to stay in place during transport and use of the apparatus 100. There is sufficient distance 224 between the second end 206 of the sublimation cartridge 222 and the second retaining screen 214 such that the sublimation cartridge 222 stays on the heat emitting end 126 of the heat source 114. Also, the attachment of the sublimation cartridge 222 to the heat emitting end 126 is such that it provides the proper air flow to reduce the possibility of an explosion and maintain combustion for those embodiments utilizing a combustion based heat source 114.

In the first embodiment, the chamber 102 is a transparent plastic dome, about 11 inches in diameter, defining an internal space 128 and having an open end 104 and a connecting end 106 which is used to connect the chamber 102 to the heat source 114. The chamber 102 may have rigid or flexible walls and edges. As shown in FIG. 1, the connecting end 106 has an entry aperture 108 through which the heat emitting end 126 of the heat source 114 protrudes into the internal space 128 of the chamber 102. A back plate 110, preferably made of metal or heavy duty plastic, is securely mounted to the connecting end 106 of the chamber 102 by one or more removable screws 112 or other mechanical fasteners. The back plate 110 in turn is securely mounted on the heat emitting end 126 of the heat source 114, thereby joining the chamber 102 to the heat source 114. The chamber 102 is shown and described as a transparent dome for convenience purpose only. It would be readily apparent to one of ordinary skill in the art to design and implement a chamber 102 having a different shape and size, and to removably attach a chamber 102 to a heat source 114.

In a second embodiment, the chamber 102 has a seal 130 around the perimeter edge of the open end 104. The seal 130 functions to further contain the vapors 306 within the internal space 128 by sealing the open end 104 against a surface on which the object 302 being examined is placed. The seal 130 is made of a foam or neoprene type material. Possible surfaces on which to use the apparatus 100 include the ground, a wall, furniture surface, vehicle surface, and the like.

Figure 3:
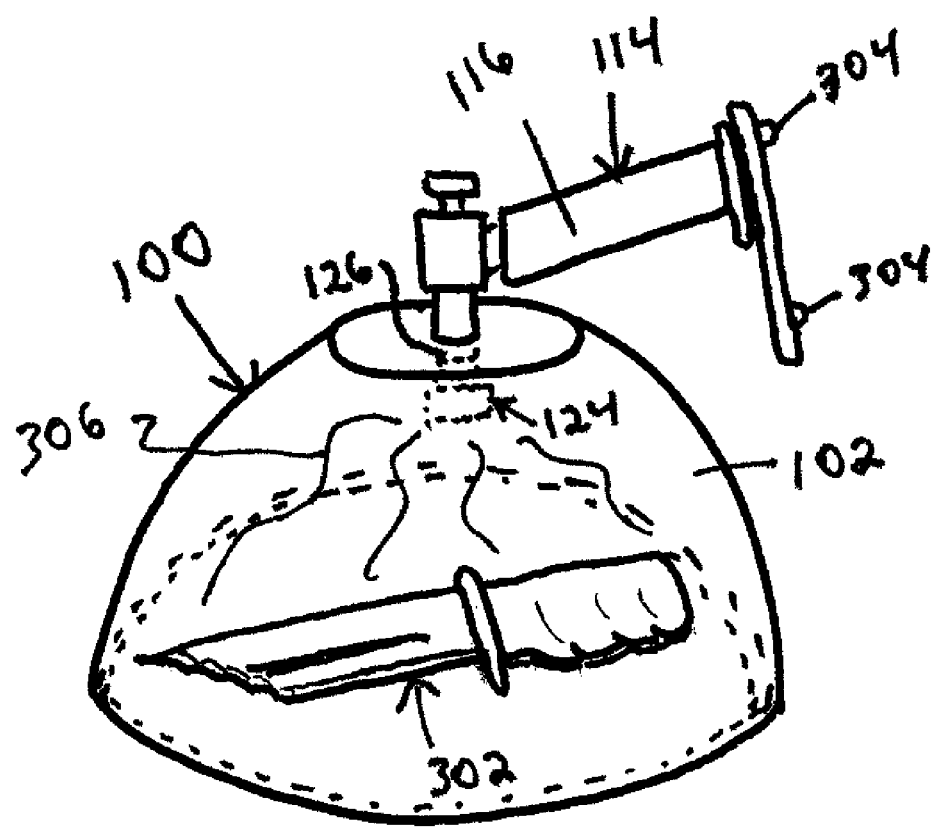
FIG. 3 is a perspective view of the apparatus developing latent fingerprints on an object.

The use and operation of the apparatus 100 is shown in FIG. 3. A user turns the on/off button 122 to activate the heat source 114 which causes the generation of heat out of the heat emitting end 126 of the heat source 114. The heat activates the cyanoacrylate disposed on the porous pad 212 which in turn generates the cyanoacrylate vapors 306. The user holds the heat source 114 by the handle 116 and places the chamber 102 over the object 302, such as a weapon (knife) or other item, being examined. Latent fingerprints start to develop within seconds because the chamber 102 contains the vapors 306 within the internal space 128 and directs the vapors 306 directly toward and around the object 302. When finished developing fingerprints on the object 302, the user returns the apparatus 100 to the resting position on the second base 120 as shown in FIG. 1.

The sublimation cartridge 222 of this first embodiment is rechargeable in that once the cyanoacrylate is exhausted, more cyanoacrylate may be deposited on the porous pad 212. Preferably, the user deposits about 6-7 drops of liquid cyanoacrylate onto the porous pad 212 through the first retaining screen 216. The cyanoacrylate may be applied to the porous pad 212 while the sublimation cartridge 222 is still connected to the heat emitting end 126 of the heat source 114, or alternatively, after the sublimation cartridge 222 is removed from the heat source 114. Regardless of how the cyanoacrylate is applied to the sublimation cartridge 222, the sublimation cartridge 222 should be in a vertical position while depositing the cyanoacrylate to prevent the cyanoacrylate from dripping off of the porous pad 212 during its drying time. After approximately three minutes of drying, the apparatus 100 is ready to use again. If the sublimation cartridge 222 was removed for the application of new cyanoacrylate, it is slide back onto the heat emitting end 126 of the heat source 114 prior to use. A recharged sublimation cartridge 222 provides approximately five to ten minutes of fingerprint developing capabilities.

Figure 5:
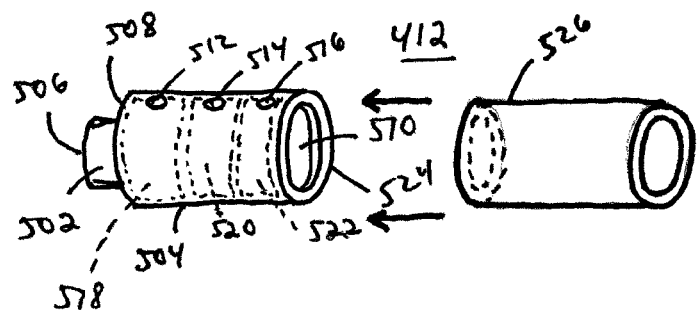
FIG. 5 is a perspective view of an alternative sublimation cartridge.
Figure 4:
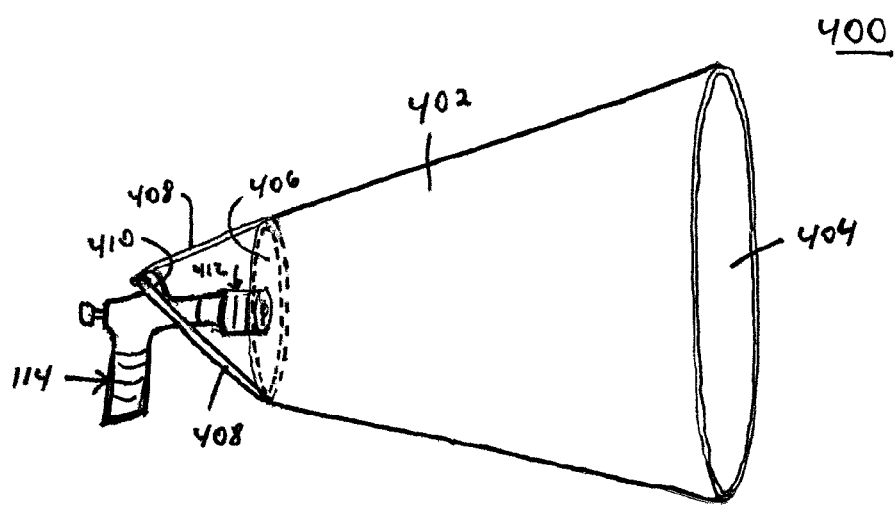
FIG. 4 is a perspective view of an alternative embodiment of the apparatus.

In a second embodiment, the sublimation system 124 is a sublimation cartridge 412 shown in FIGS. 4 and 5. In this embodiment, the sublimation cartridge 412 is an elongated hollow tube 504, defining an internal space 510, with a first end 524 adapted to be in communication with the internal space 128 of the chamber 402, and a second end 506 adapted to be removably secured to the heat emitting end 126 of the heat source 114. In one embodiment, the second end 506 is sized to be slidably attachable to the heat emitting end 126 of the heat source 114. However, in alternative embodiments, conventional connectors and/or mechanical fasteners may be used to removably secure the sublimation cartridge 412. In another alternative embodiment, as shown on FIG. 5, the sublimation cartridge 412 also has a connector portion 502 at the second end 506 which is sized and shaped to be removably mounted to the heat emitting end 126 of the heat source 114. The connector portion 502 is a smaller hollow tube having a diameter adapted to be pressure fit on the heat emitting end 126.

The sublimation cartridge 412 also has a plurality of apertures, such as first aperture 512, second aperture 514, and third aperture 516, extending through the wall of the sublimation cartridge 412 and into the internal space 510. Preferably, the first aperture 512, the second aperture 514, and the third aperture 516 are aligned along a longitudinal axis of the sublimation cartridge 412.

In one embodiment, three elements are disposed within the internal space 510 of the sublimation cartridge 412. A first element 518 is adapted for receiving and retaining water through the first aperture 512. A second element 520 is adapted for receiving and retaining a cyanoacrylate, such as a liquid or solid heat activated cyanoacrylate, through the second aperture 514. A third element 522 is adapted for receiving and retaining a sublimation dye through the third aperture 516. The three elements 518, 520, and 522 may be disposed within the internal space 510 in any order, but the described order is preferred. Also, it would be readily apparent to one of ordinary skill in the art to determine the amount of water, cyanoacrylate and sublimation dye to use with the present invention.

The sublimation cartridge 412 is preferably made of metal, ceramic, certain plastics that can withstand high temperatures, or glass. Also, the second element 520 and the third element 522 are preferably porous pads such as steel wool, ceramic fiber, granulated loose wool, or non-granulated loose wool. The first element 518 is preferably a porous insulating pad such as a ceramic insulating fire brick which can withstand high temperatures.

Upon charging the sublimation cartridge 412 with water, cyanoacrylate, and a sublimation dye, the sublimation cartridge 412 is mounted on the heat emitting end 126 of the heat source 114 as shown in FIG. 4. Also, an optional sleeve cover 526 may be slid over the sublimation cartridge 412 to further support the sublimation cartridge 412 and to cover the first, second and third apertures 512, 514, 516. A chamber 102 as shown in FIG. 1 may be used with this embodiment, or alternatively, an alternative chamber 402 is used.

In an alternative embodiment, a chamber 402 having an open end 404 and an entry aperture 406 is mounted to the heat source 114 by one or more tethers 408 attached to a flange 410 on the heat source 114 such that the first end 524 of the sublimation cartridge 412 is directly in front of, or alternatively extends into, the entry aperture 406 of the chamber 402. In operation, upon activating the heat source 114, the heat engages the sublimation cartridge 412 which generates the vapor 306 used to develop latent fingerprints as described herein.

Figure 8:
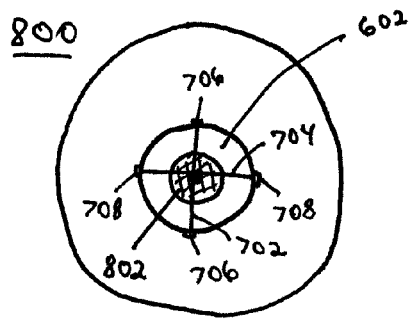
FIG. 8 is a planar bottom view of the alternative chamber with a second alternative sublimation system.
Figure 7:
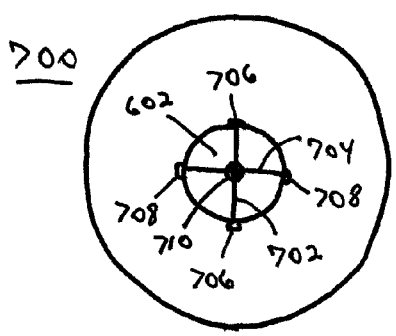
FIG. 7 is a planar bottom view of the alternative chamber with the alternative sublimation system.
Figure 6:
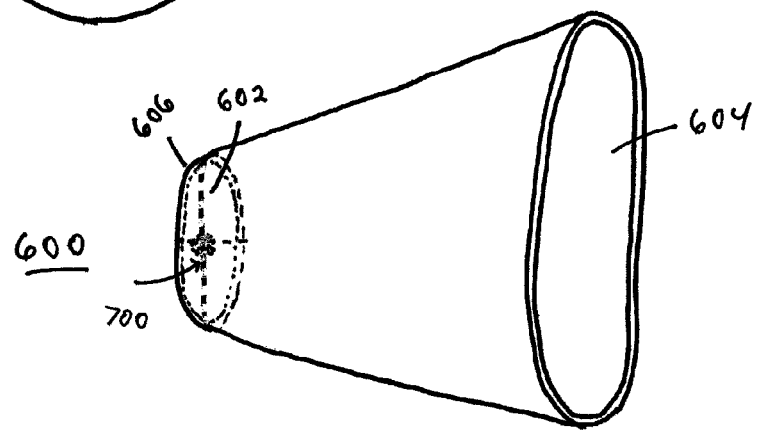
FIG. 6 is a perspective view of an alternative chamber of the present invention with an alternative sublimation system.

A third and fourth embodiment of the sublimation system 124 are shown in FIGS. 6-8 which also uses the chamber 402 shown in FIG. 4. A pair of tethers 702, 704 is connected to the edge 606 of the entry aperture 602 of a chamber 600 by mechanical fasteners 706, 708. The pair of tethers 702, 704 are each preferably a metal wire. In addition, a pair of tethers 702, 704 are used for convenience. It would be readily apparent to one of ordinary skill in the art to use one or more tethers, or a comparable means for securing the chamber 600 to a heat source 114.

In FIGS. 6 and 7, the sublimation systems 700, 800 further comprise a small porous pad 710, such as steel wool, secured to the intersection of the pair of tethers 702, 704. Alternatively, in FIG. 8, the sublimation system 800 further comprises a porous platform 802, such as a metal or plastic mesh screen, secured to the pair of tethers 702, 704 overlaying the intersection of the tethers 702, 704. Then, liquid or solid cyanoacrylate is deposited on the porous pad 710 or porous platform 802. In the case of a solid cyanoacrylate, e.g., in pellet form, the solid cyanoacrylate may be secured directly to the porous platform 802 by an adhesive, fastener, or in the curing process if the porous screen 802 is plastic. When the chamber 600 is mounted to the heat source 114, the heat emitting end 126 of the heat source 114 is aligned with and positioned immediate in front of the entry aperture 602 of the chamber 600, as well as, is preferably aligned with the porous pad 710.

In operation, upon activating the heat source 114, the heat engages the sublimation system 700, 800 and the heat transforms the cyanoacrylate into vapor within the chamber 600 thereby enabling the development of latent fingerprints.

Figure 9:
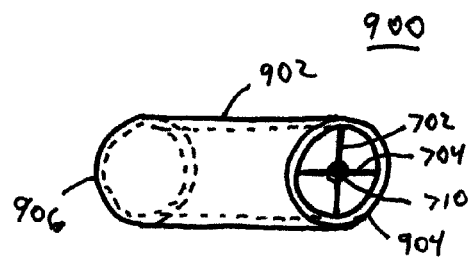
FIG. 9 is a perspective view of an alternative sublimation cartridge.

FIG. 9 is a perspective view of an alternative sublimation system 900 having a sublimation cartridge 902 having a first end 906 and a second end 904. The first end 906 is adapted to slidably attach to the heat emitting end 126 of the heat source 114. The second end 904 has the pair of tethers 702, 704 as shown in FIGS. 7 and 8. Also, shown is a porous pad 710 adapted to receive and retain the cyanoacrylate. Alternatively, a porous platform 802 may be incorporated into this sublimation cartridge 900 as described above. In operation, the sublimation cartridge 900 is used as also described above.

CONCLUSION

While various embodiments of the present invention have been described above, it should be understood that they have been presented by the way of example only, and not limitation. It will be understood by those skilled in the art that various changes in form and details may be made therein without departing from the spirit and scope of the invention as defined. Thus, the breadth and scope of the present invention should not be limited by any of the above-described exemplary embodiments.

What is claimed is:

1. An apparatus for developing latent fingerprints on objects, comprising:

a heat source connected to a conduit having a heat emitting end;

a sublimation system in communication with said heat emitting end of said conduit, said sublimation system adapted for receiving a cyanoacrylate that transitions to vapor upon activation of said heat source; and a chamber having a connecting end in communication with said sublimation system, said conduit extending into an internal space of said chamber, said internal space adapted to receive and contain at least a portion of an object, and an open end for receiving the object;

wherein said heat source is outside said internal space;

wherein said sublimation system is a sublimation cartridge having a first end in communication with said internal space of said chamber, a second end in communication with said heat emitting end of said conduit, and an outer wall of said sublimation cartridge between said first end and second end and containing a porous pad adapted to receive said cyanoacrylate, and wherein said sublimation cartridge is removably attachable to said heat emitting end of said conduit.

2. The apparatus of claim 1, wherein said heat source is selected from the group consisting of a pressurized fuel system, a torch system, a forced air heat system, and an electric heat system with a fan.

3. The apparatus of claim 1, wherein said porous pad is a material selected from the group consisting of steel wool, ceramic fiber, granulated loose wool, and non-granulated loose wool.

4. The apparatus of claim 1, wherein said sublimation cartridge further comprises a head, a throat, and a means for retaining said porous pad within said sublimation cartridge.

5. The apparatus of claim 1, wherein said sublimation cartridge further comprises one or more tethers attached to said first end of said sublimation cartridge, wherein said porous pad is disposed on said one or more tethers.

6. The apparatus of claim 1, wherein said cyanoacrylate is selected from the group consisting of a liquid cyanoacrylate, a solid cyanoacrylate, and a cyanoacrylate adhesive.

7. The apparatus of claim 1, wherein said chamber is a dome shape.

8. The apparatus of claim 1, wherein said chamber is transparent.

9. The apparatus of claim 1, wherein said chamber has a seal on an edge of said open end for sealing said internal space against a surface.

10. The apparatus of claim 1, further comprising a means for coloring the latent fingerprints.

11. The apparatus of claim 10, wherein said means for coloring is a sublimation dye introduced to said sublimation system.

12. The apparatus of claim 1, wherein said outer wall of said sublimation cartridge contains a first element adapted for receiving said porous pad, a second element adapted for receiving water, and a third element adapted for receiving a sublimation dye.

13. The apparatus of claim 12, wherein said outer wall of said sublimation cartridge is made of a material selected from the group consisting of: metal, ceramic, and glass.

14. The apparatus of claim 12, wherein said second element and said third element are selected from the group consisting of a porous pad, and an insulating pad.

* * * * *